United States Patent
Gaurav et al.

(10) Patent No.: US 9,741,234 B2
(45) Date of Patent: Aug. 22, 2017

(54) METHOD AND SYSTEM FOR BROADCASTING A PANIC ALERT NOTIFICATION

(71) Applicant: HONEYWELL INTERNATIONAL INC., Morristown, NJ (US)

(72) Inventors: Galib Gaurav, Bihar (IN); Sunil Parisi, Pradesh (IN); Chaithra Mandanna K, Karnataka (IN); Nikhil Scaria, Kerala (IN); Kamalakannan Subramaniyan, Pondicherry (IN); Divyashree Krishnamurthy, Karnataka (IN)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 14/704,089

(22) Filed: May 5, 2015

(65) Prior Publication Data
US 2015/0332581 A1 Nov. 19, 2015

(51) Int. Cl.
G08B 25/01 (2006.01)
G08B 21/02 (2006.01)
H04H 20/59 (2008.01)
G08B 25/00 (2006.01)
A61B 5/11 (2006.01)

(52) U.S. Cl.
CPC .......... *G08B 25/016* (2013.01); *G08B 21/02* (2013.01); *G08B 25/005* (2013.01); *H04H 20/59* (2013.01); *A61B 5/1112* (2013.01); *G08B 21/0269* (2013.01); *G08B 21/0272* (2013.01)

(58) Field of Classification Search
USPC .................................. 340/539.13; 455/404.2
See application file for complete search history.

(56) References Cited

U.S. PATENT DOCUMENTS

| | | | |
|---|---|---|---|
| 9,232,378 B2 * | 1/2016 | Khosla | H04W 4/22 |
| 2014/0118140 A1 * | 5/2014 | Amis | G08B 25/08 340/539.13 |
| 2015/0288797 A1 * | 10/2015 | Vincent | H04M 1/72538 455/404.2 |

* cited by examiner

*Primary Examiner* — Leon-Viet Nguyen
(74) *Attorney, Agent, or Firm* — Husch Blackwell LLP (57) ABSTRACT

The present invention relates to a method and system for broadcasting a panic alert notification in a communication network comprising a primary user and at least one secondary user. The method comprises the steps of receiving data relating to a panic alert and processing information and geo-location of the primary user. Further, a list of one or more secondary users to be notified of the primary user's emergency situation is determined and a broadcast alert message is transmitted to the one or more secondary users. The step of determining a list of one or more secondary users comprises determining a search range criteria in the vicinity of the geo-location of primary user, identifying a list of secondary users within the search range criteria and determining one or more first level and second level secondary users by mapping the list of secondary users with a list of users known to the primary user.

15 Claims, 4 Drawing Sheets

METHOD AND SYSTEM FOR BROADCASTING A PANIC ALERT NOTIFICATION

FIELD OF THE INVENTION

The present invention relates to a personal safety notification method and system and particularly, to a method and system for initiating and broadcasting alert messages to at least two levels of users based on the geo-location of the user initiating the alert.

BACKGROUND

The need tier assistance during an emergency situation is a real issue of concern in today's day and age, especially for individuals who may not be able to protect themselves in an adverse situation. In certain countries like the United States of America, a source of help in the event of an emergency is facilitated by the "911" telephone system, which connects the caller to an operator who is trained to identify a number of emergency situations and has access to communication equipment to contact the police, ambulance, fire department and the like to direct external assistance in case of an emergency. Similar facilities are available in other countries as well; however, in countries like India, such facilities are yet to be implemented or may not be feasible given the lack of adequate infrastructure development. Accordingly, in India, and other countries in South Asia and Africa, a person facing an emergency situation and in need of medical or security assistance has to resort to the more conventional ways of defending himself; screaming for help or combating a situation with no assistance. In certain instances, although third parties may be willing and able to provide assistance, many situations are not responded to in a timely manner, or at all, because the individual in need of assistance is unable to get to a telephone and/or cannot reach others for help.

In still other cases, contacting a third party using a telephone (wireless or otherwise) may not be feasible given that the situation at hand may be hostile. Therefore, manually making a phone call, taking a picture, and/or a video can be prevented by a perpetrator because it will be obvious what the potential victim is doing or attempting to do. This can, additionally, escalate the situation and may even put the potential victim in grave danger. Furthermore, even if the potential victim is able to initiate a call via a wireless device, if he/she is unable to communicate the location where the incident is taking place, then diverting help to the potential victim can be very difficult, if not impossible, due to the uncertainty in determining the crisis location.

Some technology is available that is useful for provisioning for emergency services. For example, newer wireless devices are equipped with hardware/software to determine their locations using Global Positioning Services (GPS) and/or other positioning technologies. Some software based applications have been implemented to accurately determine the geo-location of the wireless device. In other instances, applications have been developed that will initiate a call and/or send a message to a selected list of individuals specifically identified by the potential victim. For example, in India, mobile based applications such as 'Vithu' have been introduced, which is intended to aid women during an emergency. The application sends an SOS message to previously identified people listed in the application who will be contacted when the user clicks the power button twice indicating an unsafe situation. However, such applications and technologies cannot guarantee that all users will be reachable and more importantly, such applications do not account for the distance that is present between the potential victim pre-identified helpers, thereby greatly reducing the effectiveness of available solutions.

Thus, existing methods and systems do not have the ability to contact known individuals in the immediate area around the potential victim. Moreover, existing methods and systems do not have the ability to contact the general public or emergency service professionals who may be able to provide assistance and are in the immediate area around the potential victim. Accordingly, there is a need for achieving personal security through a panic alert notification method and system which calculates the geo-location of a potential victim or a distressed user; identifies a first level of secondary users who are known to the distressed user and are in the vicinity; identifies a second level of secondary users who may or may not be known to the distressed user and are in the vicinity of the distressed user; and subsequently communicates a panic alert to the first and second level of secondary users by transmitting information relating to the emergency and the location of the incident.

SUMMARY

It is an objective of the present invention to provide a method and system for initiating and broadcasting alert messages to at least two levels of users based on the geo-location of a distressed user wherein said system comprises a wireless device being operated by a distressed user and at least one secondary wireless device which is connected via a communication network to communication servers, and a central panic alert system which receives the information from the distressed user, selectively identifies the first and second level of secondary users, formats the necessary broadcast message and transmits the broadcast alert. The central panic alert system comprises modules, for example, a receiver module, a processing module, one or more user profile management modules, and one or more databases. The system may further comprise, a dynamic location determination module, a secondary user determination module and a panic alert transmitter module which are configured to identify a first level of secondary users who are known to the distressed user and are in the vicinity; selectively identify a second level of secondary users who may or may not be known to the distressed user and are in the vicinity of the distressed user; and transmit a broadcast alert message to a first and second level of secondary users who can assist the distressed user.

It is yet another objective of the present invention to provide the method for broadcasting alert messages to one or more individuals/secondary users when a distressed user is in an emergency situation, said method comprising triggering a panic alert though a device; receiving the alert at the central panic alert system; processing the alert to identify the distressed user's profile and current geo-location information; dynamically identifying all users within a range of the distressed user's geo-location; extracting a first level of contacts or secondary users; selectively extracting a second level of contacts or secondary users, each first and second level secondary user being within the permitted range of the distressed user; generating a list of all secondary users to be contacted; and transmitting a broadcast alert message to each of the selected first and second level contacts/secondary users.

In another objective of the present invention, the system identifies and extracts information related to a third level of secondary users, the emergency services professionals like the police, emergency medical services, hospitals, fire department etc. within the permitted range of the distressed user and transmits a broadcast alert message to each of the selected third level secondary users. It is yet another objective of the present invention to provide the method for iteratively re-transmitting the broadcast alert message to an updated list of first, second and third level secondary users after a user or system defined time interval from the first broadcast alert message.

In yet another objective of the present invention to provide a method of registering a user with the central panic alert system, said method comprising the steps of accessing the central panic alert system, creating an account on the said system, providing one or more information, said information may include at least name, address, identification information, photograph, contact details, social networking account and profile details.

To foregoing and other objects, features and advantages of the invention will be apparent from the following detailed description in conjunction with the drawings described hereinafter. It is appreciated that these drawings depict only typical embodiments of the invention and are therefore not to be considered limiting in its scope.

DETAILED DESCRIPTION OF THE PRESENT INVENTION

Figure 1:
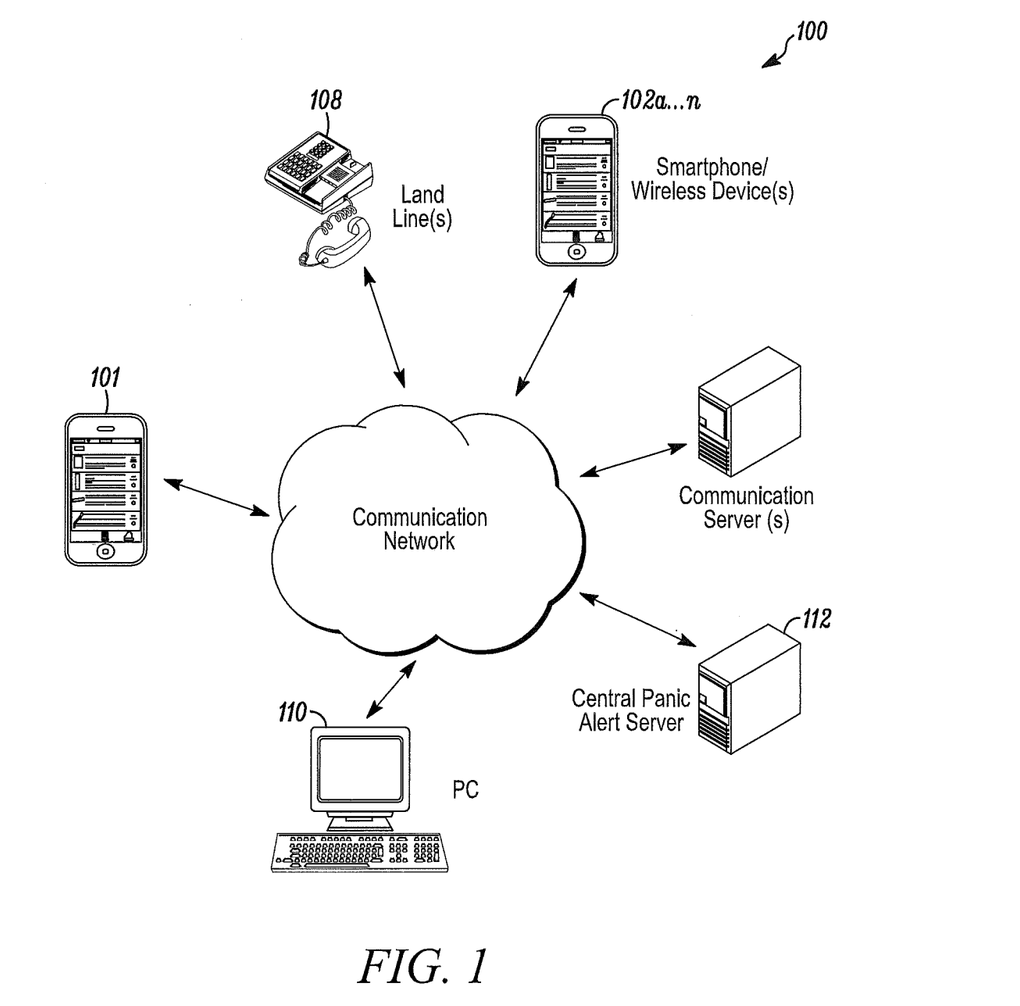
FIG. 1 illustrates a central panic alert system according to an embodiment of the present invention.

FIG. 1 illustrates an exemplary panic alert system 100 in accordance with the present invention. The system (100) comprises at least one primary wireless device (101) and at least one secondary wireless device (102a . . . n) which are communicatively connected to communication servers and a Central Alert System (CAS) (112) via a communication network. As known to a person skilled in the art and as illustrated in FIG. 1, communication servers may also be connected to one of more land lines (108), one or more PCs (110). The wireless device is preferably a smart phone running an operating system for example Java, Android, Windows Mobile, Java ME, iPhone, or Symbian. Examples of wireless devices include a traditional cell phone or other wireless communications device with computing capability such as a smart phone, tablet, PDA, iPhone, etc. The wireless device may also be a tablet such as an iPad, a car-mounted system such as an in-dash navigation system, a laptop, or a specific device for example a transceiver designed primarily to provide emergency safety notification. The primary device (101) which is in use by a distressed user initiates a panic alert which is transmitted via the communication network to the CAS. The CAS receives the panic alerts and processes the information associated with the alert. The CAS further selectively identifies the secondary wireless devices (102a . . . n) associated with a first and second level of secondary users. The CAS transmits a broadcast alert to the secondary wireless devices (102a . . . n) in accordance with the methods of the present invention. In an alternate embodiment, the CAS further selectively identifies secondary wireless devices (102a . . . n) associated with a third level of secondary users. The CAS then transmits a broadcast alert to the secondary wireless devices (102a . . . n) in accordance with the methods of the present invention. In yet another embodiment, the CAS (112) configured to iteratively re-transmit the broadcast alert message to an updated list of first, second and third level secondary users after a user or system defined time interval from the first broadcast alert message.

Figure 2:
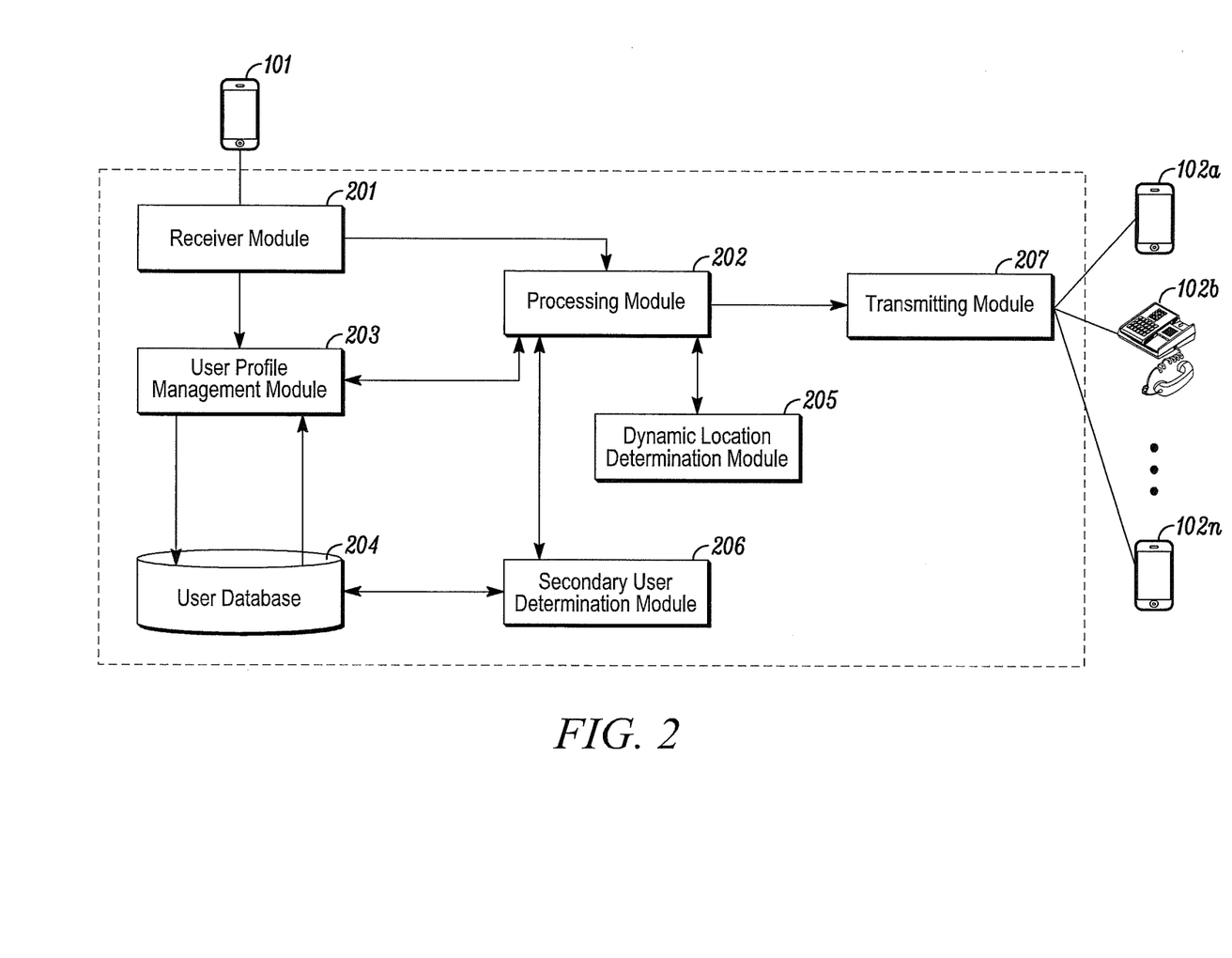
FIG. 2 illustrates a detailed modular view of the central panic alert system according to an embodiment of the present invention.

Further embodiments of the panic alert system (100) will be described with reference to FIG. 2. As illustrated in FIG. 2, the Central Alert System (CAS) (112) receives a panic alert from a distressed user, the primary user, via a primary wireless device (101). In an exemplary embodiment, the CAS comprises a receiver module (201), a processing module (202), a user profile management module (203), and a database (204). The CAS (112) further comprises a dynamic location determination module (205) operatively coupled with the processing module (202) to process and identify users within certain geo-location parameters. Further, the CAS (112) comprises a secondary user determination module (206) and a transmitter module (207).

In the exemplary embodiment, the CAS receiver module (201) is configured to receive a panic alert from the distressed user wherein the panic alert is initiated through a primary wireless device (101). The alert from the distressed user can be transmitted to receiver module (201) by a wireless or wired communication channel as a data packet or other communication schemes known to a person skilled in the art. In a preferred embodiment, the distressed user is registered with the CAS (112) as described in relation to FIG. 4 below. In the exemplary system, registration includes providing information pertaining to the distressed user comprising, for example, name, contact information, address information, social network profile information and other necessary permissions, which would enable the CAS (112) to create, store and access the profile of the primary and secondary users at the appropriate time, to extract and process contact information of the users and other relevant information as required by the CAS (112) to transmit the broadcast panic message to the secondary users.

In an embodiment, the distressed user may initiate the panic alert to the CAS (112) by means of one or more communication modes, said modes may include dialing a predefined number, or pressing a default key or input, combination of keys or inputs, or based on a predefined motion of the wireless device (shaking etc.). Such initiation of a panic alert is generally known in the art and can be alternatively customized by the user to match his/her preference. In an embodiment, where the distressed user possesses a wireless device such as a smartphone, an application may be installed on said device, which provides the user a customized option of triggering a panic alert.

In the exemplary situation, when a distressed user is in an emergency situation, he/she initiates a panic alert, which is transmitted by the primary wireless device (101) to the receiver module (201) of the CAS (112). Upon receiving the panic alert, the data associated with the alert is extracted and transmitted to the processing module (202). The processing module (202), in conjunction with a user profile management module (203) and a user database (204), retrieves and processes the relevant information of the distressed user which comprises, for example, name, address, picture (if provided during registration) and any other information sufficient to identify the distressed user. In this embodiment, the information associated with the user is stored in a database (204) and is accessed through a processor coupled with memory (not shown).

Further, the processing module (202) is coupled to a dynamic location determination module (205) which retrieves the current geo-location of the distressed user using the data provided in the panic alert message processed by the processing module (202). In an embodiment, the current geo-location includes the latitude and longitudinal location of the distressed user determined by, for example, a Global Positioning system (GPS) of the communication network. Other options for determining the geo-location of a user are known and can be applied in a manner known to a person of ordinary skill in the art and include creating a visual map of the location based on the latitude and longitudinal location of the distressed user determined by the GPS. In an alternate embodiment, the dynamic location determination module (205) may be an operative part of the processing module (202).

The dynamic location determination module (205), based on range criteria defined by the processing module (202), retrieves a list of all users currently within an acceptable range of the distressed user and provides the same to the processing module (202). For example, in an exemplary embodiment, the secondary users are determined based on their location being not more than 5 kilometers radial distance from the geo-location of the distressed user. The dynamic list of all users within a certain geo-location range can comprise all registered users that meet the criteria and any other users who can be identified by integrating the CAS with external resources and third party applications and technologies.

The processing module (202) is further operatively coupled with the secondary user determination module (206) to retrieve and process the list of all secondary users to be contacted with a broadcast alert message. The secondary user determination module (206) is coupled to a user database (204), a processor and memory to retrieve and processes information related to a first and second level of the secondary users as described below. In this embodiment, the secondary user determination module (206) based on the information relating to the distressed user received from the processing module (202) which comprises a list of all users currently within an acceptable range of the distressed user, retrieves a list of users who are known to the distressed user and are identified as the first level secondary users by the distressed user during the registration process. In an embodiment, the extracted contacts may include a sub set of the distressed user's phonebook contacts and social networking contacts. In another embodiment, the secondary user determination module (206) is provided permission to access the social networking account of distressed user to retrieve a list of associated first level contacts from a social networking website.

The secondary user determination module (206) further accesses the user database (204) and, based on the predetermined range, in conjunction with the location determination module (205) extracts the list of contacts that are unknown to the distressed user but are in the vicinity of the distressed user. These users are identified as the second level secondary users by the CAS. In a further embodiment, determination of the second level secondary users is performed selectively based on the nature of the panic alerts received by the distressed user and/or user defined criteria for informing/not informing a second level of secondary users.

Upon determination of the first and second level secondary users who are in close vicinity to the distressed user, the processing module (202) prepares a final list of secondary users who are to be contacted with a broadcast alert message. Then, a broadcast alert message is generated and the same is transmitted via the transmitting module (207), to one or more secondary devices (102a . . . n) associated with each of the secondary users. In an embodiment, the broadcast alert message includes a short message or an automated telephone call identifying the distressed user's information and current location.

In a further embodiment, the transmitting module (207) is configured to generate a follow-up alert message, after a certain time interval, to secondary users previously identified by the secondary user determination module (206) and any other users that may have now come within the vicinity of the distressed user. In this embodiment the secondary user determination module (206) re-processes the information to identify any additional first or second level secondary users that may now be in the range of notification.

Figure 3:
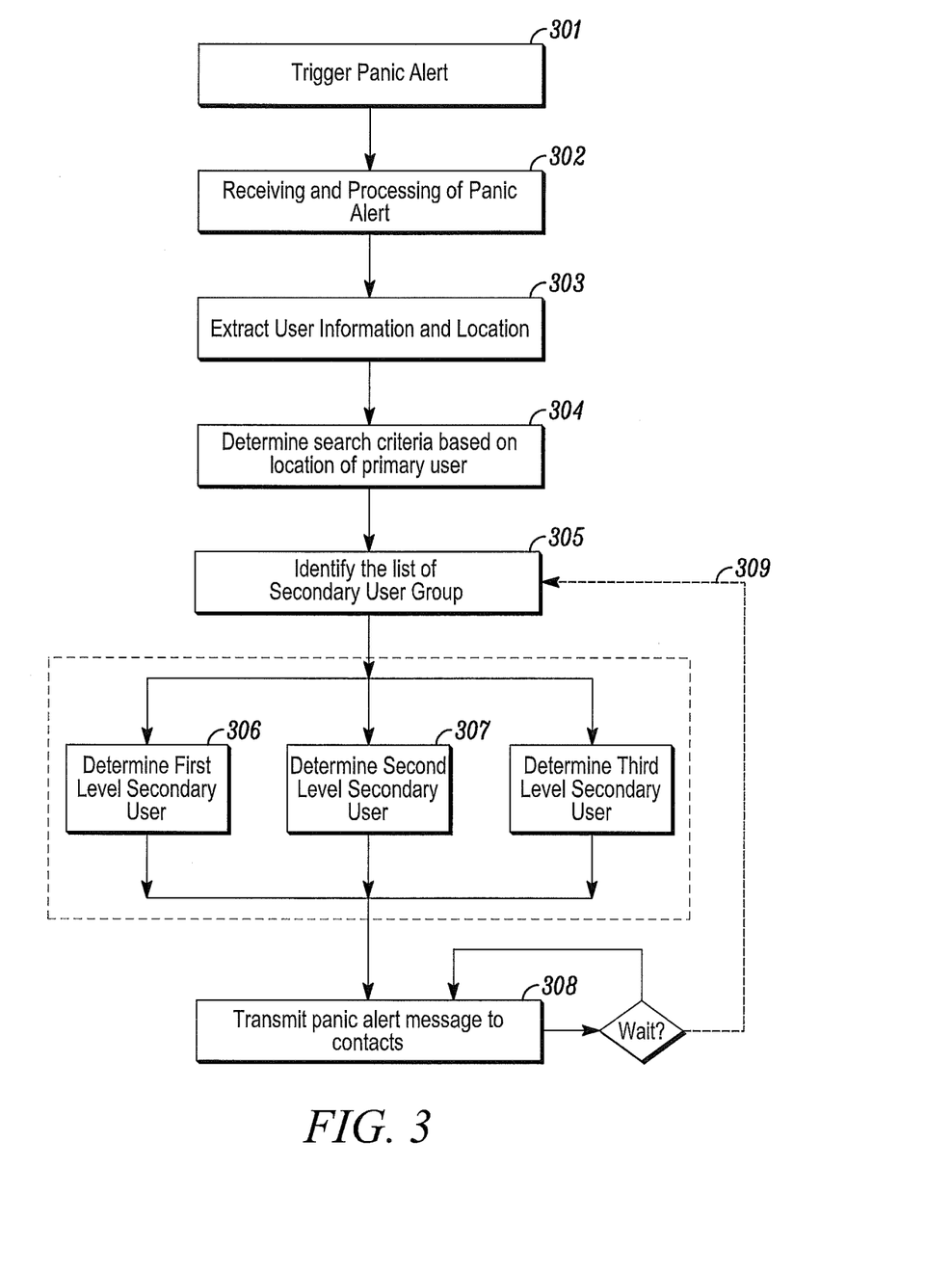
FIG. 3 illustrates a method steps for generating panic alert according to an embodiment of the present invention.

FIG. 3 illustrates exemplary steps of generating the broadcast alert message to one or more secondary users when a distressed user is in an emergency situation in accordance with a preferred embodiment of the present invention. In step 301, when a primary user (or distressed user) counters an emergency situation, the distressed user triggers a panic alert though a wireless device or any other means known to a person skilled in the art. The panic alert as generated by distressed user may be one of short message or a call initiated by the wireless device of distressed user. In step 302, the panic alert message is received as a data packet at the Central Alert System (CAS) and is processed further to identify the distressed user's profile and current location information. In one embodiment, the related information of the distressed user is mapped by a unique identifier such as mobile phone number or any combination of other unique identifiers (e.g., an instant messenger (IM) ID, wireline phone number, unique device ID, etc) is extracted from the user database.

In step 303, the distressed user's profile is accessed to extract information and any permissions relating to the primary user which may include information regarding all entries in the distressed user's phonebook list and/or contacts who are associated with the distressed user via social networking services, for example, facebook, twitter or any other social networking services currently prevailing in the communication network. In a further embodiment, the CAS may be enabled to utilize a third party services to extract the contact list of distressed users, wherein the third party services separately maintains the list of the first and second group of contacts.

In step 304, the user information and geo-location is processed to determine the secondary user search range. In this step, using a predefined search range criteria, for example, a predefined distance of 5 kilometers from the vicinity of the distressed user, a search criteria is determined. In other embodiments, the predefined search criteria are configurable depending upon on the population density, crime index, danger level etc.

In step 305, a list of all secondary users within the search range parameters of the previous step are dynamically identified by the CAS. In this step, the location of each of the secondary users is analysed using Global Positioning Services and/or other positioning technologies to identify the location. The CAS may be enabled to utilize a third party services for processing dynamic location information of secondary users. In alternate embodiments, the secondary user list created based on the dynamic location of the users can comprise users who may not be registered with the CAS system and such a list can be created by interfacing with third party services. If the system is unable to identify any secondary users as a result of the dynamic location search in the search vicinity radius, the system may be alternatively configured to expand the search radius to identify one or more first and second levels of contacts. In an another exemplary embodiment, where the current location of the distressed user is an isolated place, the system is pre-configured to search the first and second group of contacts with expanded radius near the vicinity of distressed user.

In an alternate embodiment, in Step 305*a* (not shown), the list may include a third level of secondary users, said users being available emergency services such as police station, hospital or emergency aid services available in the vicinity of the distressed user.

In step 306, the distressed user's profile information and the secondary user list from the previous step are analyzed and processed to map a first level of secondary users who are known to the distressed user. These first level secondary users can be based on a predefined list created by the distressed user, or be part of their phonebook contact list or their contacts from their social networking accounts. In Step 307, a second level of secondary users is mapped and comprises all users who are registered with the CAS and have agreed, for example, to help a person in case of an emergency situation. In other embodiments, the secondary users may not be registered with the CAS but can be obtained through third party services.

In Step 308, a broadcast alert message is created and transmitted to the first and second levels of the secondary users who are in close vicinity to the distressed user. The broadcast alert message will be triggered and transmitted to notify, contact or communicatively connect each and every member of the first and second contacts (102*a*, . . . , *n*) in a two-way, broadcast, or multiparty communication, for example, by phone call, Internet chat, conference call, group e-mail, SMS or other text-based message, or other real-time or asynchronous communication.

In a further embodiment, in Step 309, a follow-up broadcast alert message is iteratively re-transmitted to the secondary users at certain pre-determined intervals according to the configuration of the panic alert system. By way of example, the CAS may be configured to send reminders in 5 minute intervals to the first and second level secondary users. In an alternate embodiment, the CAS may be configured to send reminders in 5 minute intervals to the first and second level secondary users after repeating steps 305, 306 and 307 to identify any new secondary users to be added to the list and/or secondary users to be removed from the list due to a change in their geo-location. In a further embodiment, the CAS may be configured to send reminders in 5 minute intervals to an additional third level of secondary users comprising the police, emergency medical services, hospitals, fire department or the like. The period of time for sending the panic alert again may be configured by a subscriber, end-user, or service provider. Further, the time periods may be set different for the different groups.

Figure 4:
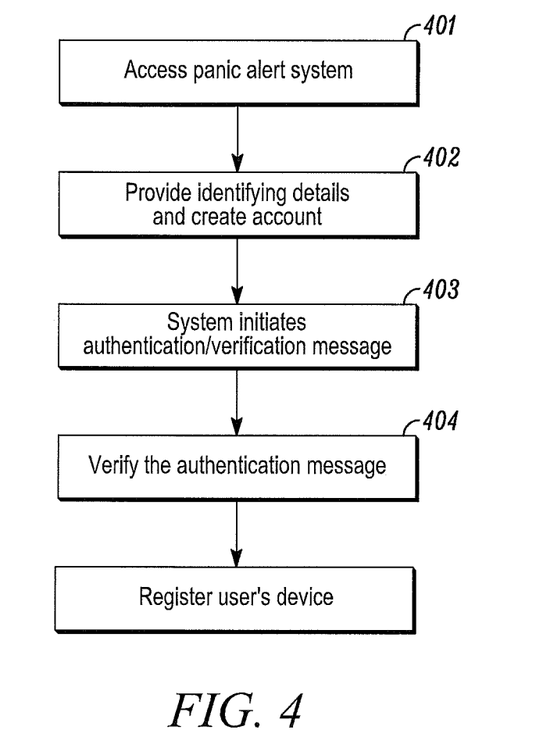
FIG. 4 illustrates a method of registering a user on the central panic alert system.

FIG. 4 illustrates an exemplary registration of a user of the panic alert. In Step 401, a user accesses the central panic alert system though one or more communication means, said communication means includes web application, internet, VOIP, IVR and any other means known to a person skilled in the art. In Step 402, the user creates an account on the said system and provides one or more information, said information may include at least name, address, identification information, photograph, contact details, social networking account and profile details. In Step 403, the system initiates a verification message to the registering user to confirm the willingness of the user to register on said system. In Step 404, the user verifies the registration on the said system and a user account is created.

In one embodiment, the CAS collects additional information from the user, such as emergency contacts, height, weight, age, gender, relevant medical information, alternate addresses (e.g., a address different than the user's address), or photographs of the user. User-provided information may be in any of a variety of formats, including text, images, and audio or video files. The user is also prompted to accept the terms and conditions of use associated with CAS for example access to social networking sites and/or other third party applications and to define data sharing rules and access permissions.

In an embodiment, the distressed user may be configured to activate or deactivate access to groups of contacts as identified above depending upon the level of emergency.

In a preferred embodiment, any person(s) including the user may during registration with the CAS, additionally opt to be notified as a second level secondary user.

In a preferred embodiment, the wireless device such as smartphone, which has access to internet, may download an application to be installed on the device. The downloading and installation of application creates a shortcut to emergency services by way creating a predefined button or in case of touch screen phones, an icon. During the emergency, the distressed user may initiates panic alert by pressing the icon/predefined button or any other means known to a person skilled in the art.

In a further embodiment, the central panic alert system may be configured to initiate a verification message to the distressed user, to identify whether the panic alert has been generated inadvertently. Upon receiving the verification message, the user may confirm the initiation of the panic alert before the central panic alert system starts the processing of the user's profile and information.

While preferred embodiments of the present subject matter have been described, it is to be understood that the embodiments described are illustrative only and that the scope of the invention is to be defined solely by the appended claims when accorded a full range of equivalence, many variations and modifications naturally occurring to those of skill in the art from a perusal hereof.

We claim:

1. A method for broadcasting alert messages in a communication network comprising a primary user and a plurality of secondary users, said method comprising the steps of:

receiving a panic alert initiated by the primary user in an emergency situation;

processing information relating to the primary user, the panic alert, and a current geo-location of the primary user;

determining a search range criteria;

identifying a first set of the plurality of secondary users within the search range criteria of the current geo-location of the primary user at a first time;

determining a first level of the plurality of secondary users by mapping the first set of the plurality of secondary users with a first list of the plurality of secondary users, wherein each of the plurality of secondary users included in the first list of the plurality of secondary users is associated with the primary user;

determining a second level of the plurality of secondary users by mapping the first set of the plurality of secondary users with a second list of the plurality of secondary users, wherein each of the plurality of secondary users in the second list of the plurality of secondary users have agreed to be notified with a first of the broadcast alert messages;

transmitting the first of the broadcast alert messages to the first list of the plurality of secondary users and the second list of the plurality of secondary users;

identifying a second set of the plurality of secondary users within the search range criteria of the current geo-location of the primary user at a second time after a predetermined time interval after transmitting the first of the broadcast alert messages, wherein the second set of the plurality of secondary users includes a secondary user that is within the search range criteria of the current geo-location of the primary user at the second time but was not within the search range criteria of the current geo-location of the primary user at the first time; and identifying a selected one of the plurality of secondary users included in the second set of the plurality of secondary users and not included in the first set of the plurality of secondary users.

2. The method as claimed in claim 1, further comprising registering the primary user, wherein registration of the primary user includes providing the information relating to the primary user.

3. The method as claimed in claim 2, wherein the first level of the plurality of secondary users comprises a first of the plurality of secondary users identified by the primary user as a first level contact during the registration of the primary user.

4. The method as claimed in claim 3, wherein the first level of the plurality of secondary users comprises phonebook contacts of the primary user and/or social networking contacts of the primary user.

5. The method as claimed in claim 1, wherein the second level of the plurality of secondary users comprises a first of the plurality of secondary users registered with a panic alert notification system.

6. The method as claimed in claim 1, wherein the second level of the plurality of secondary users comprises a first of the plurality of secondary users registered with a third party system.

7. The method of claim 1, further comprising:
identifying a third set of the plurality of secondary users within the search range criteria of the current geo-location of the primary user after the predetermined time interval after transmitting the first of the broadcast alert messages to create a third list of the plurality of secondary users; and
after the predetermined time interval, retransmitting a second of the broadcast alert messages to the third list of the plurality of secondary users.

8. The method as claimed in claim 7,
wherein said third set of the plurality of secondary users comprises one of police, emergency medical services, a fire department, or a hospital.

9. The method as claimed in claim 1, wherein the first of the broadcast alert messages comprises at least one of a short message service (SMS), a telephone call, or interactive voice services.

10. The method as claimed in claim 1, wherein the search range criteria includes a predefined distance within the current geo-location of the primary user.

11. A panic alert notification system for transmitting a first broadcast panic message from a primary user to a plurality of secondary users in a communication network, said system comprising:
a memory for storing first information;
a database for storing and accessing the first information;
a receiver module that receives and extracts data related to the first broadcast panic message generated by the primary user;
a processing module configured to determine identity information relating to the primary user and a current geo-location of the primary user and to generate the first broadcast panic message;
a secondary user determination module to determine a first set of the plurality of secondary users to be notified with the first broadcast panic message at a first time, wherein the first set of the plurality of secondary users is determined to be within a search range criteria of the current geo-location of the primary user, wherein the first set of the plurality of secondary users includes a first list of the plurality of secondary users who are associated with the primary user, wherein the secondary user determination module is coupled with the processing module and is configured to determine a first level the plurality of secondary users by mapping the first set of the plurality of secondary users with the first list of the plurality of secondary users, and wherein the secondary user determination module is configured to determine a second level of the plurality of secondary users by mapping the first set of the plurality of secondary users with a second list of the plurality of secondary users who have agreed to be notified with the first broadcast panic message; and
a transmitting module coupled with the processing module to receive and transmit the first broadcast panic message to the first level of the plurality of secondary users and the second level of the plurality of secondary users,
wherein the secondary user determination module identifies a second set of the plurality of secondary users determined to be within the search range criteria of the current geo-location of the primary user at a second time after a predetermined time interval after the transmitting module transmits the first broadcast panic message,
wherein the transmitting module retransmits the first broadcast panic message after the predetermined time interval to the second set of the plurality of secondary users, and
wherein the second set of the plurality of secondary users includes a secondary user that is within the search range criteria of the current geo-location of the primary user at the second time but was not within the search range criteria of the current geo-location of the primary user at the first time.

12. The system as claimed in claim 11, further comprising a registration module for registering the primary user to the panic alert notification system.

13. The system as claimed in claim 12, wherein the first level of the plurality of secondary users comprises a first of the plurality of secondary users identified by the primary user as a first level contact during registration.

14. The system as claimed in claim 11, wherein the first level of the plurality of secondary users includes phonebook contacts of the primary user and/or social networking contacts of the primary user.

15. The system as claimed in claim 11, wherein the secondary user determination module is configured to determine a third level of the plurality of secondary users to be notified with the first broadcast panic message, and wherein said third level of the plurality of secondary users comprises one of police, emergency medical services, a fire department, or a hospital.

\* \* \* \* \*